United States Patent [19]

Ben-Nasr et al.

[11] Patent Number: 5,338,575

[45] Date of Patent: Aug. 16, 1994

[54] PROCESS FOR THE QUASI-CONTINUOUS DECAFFEINATION OF RAW COFFEE

[75] Inventors: Hedi Ben-Nasr, Gelsenkirchen-Resse; Hubert Coenen, Essen, both of Fed. Rep. of Germany

[73] Assignee: Kohlensäure-Werke Rud.Buse GmbH & Co., Bad Hönningen, Fed. Rep. of Germany

[21] Appl. No.: 57,014

[22] Filed: May 5, 1993

Related U.S. Application Data

[63] Continuation of Ser. No. 899,042, Jun. 16, 1992, abandoned, which is a continuation of Ser. No. 639,203, Jan. 9, 1991, abandoned.

[30] Foreign Application Priority Data

Jan. 10, 1990 [DE] Fed. Rep. of Germany ....... 4000474

[51] Int. Cl.$^5$ .................................................. A23F 5/20
[52] U.S. Cl. .................................................. 426/427
[58] Field of Search ................................... 426/427, 428

[56] References Cited

FOREIGN PATENT DOCUMENTS

3318317A1 11/1984 Fed. Rep. of Germany .
3713953A1 12/1987 Fed. Rep. of Germany .

*Primary Examiner*—Joseph Golian
*Attorney, Agent, or Firm*—Spencer, Frank & Schneider

[57] ABSTRACT

A process for decaffeinating raw coffee by selective extraction of the caffeine by means of a solvent that is liquid under normal conditions. Raw coffee beans are extracted for between one and several hours by means of a liquid solvent that is comprised of water and that has been saturated with carbon dioxide or other suitable gas or gas mixture at a temperature of between about 20° C. and 110° C. and a pressure of between about 30 bar and 300 bar to provide a charged liquid solvent. The pressure is reduced abruptly or within a few minutes to a pressure between about 1 bar and 10 bar to expand the raw coffee beans. The expanded raw coffee beans are rinsed in the liquid solvent for a period of between a few minutes and two hours. The expanded raw coffee beans are dried to reduce the water content to that required for subsequent roasting, and the decaffeinated and pre-dried raw coffee beans are then roasted, after which the caffeine is selectively separated from the charged liquid solvent and the caffeine is recovered in pure crystalline form.

15 Claims, 1 Drawing Sheet

PROCESS FOR THE QUASI-CONTINUOUS DECAFFEINATION OF RAW COFFEE

This is a continuation of application Ser. No. 07/899,042, filed Jun. 16, 1992 now abandoned, which is a continuation of application Ser. No. 07/639,203, filed Jan. 9, 1991 now abandoned.

BACKGROUND OF THE INVENTION

The present invention relates to a process for decaffeinating raw coffee in which the caffeine is selectively separated from the raw coffee with the aid of a liquid solvent, i.e., a solvent which is liquid under normal conditions (1 bar and 20° C.), which is saturated or even supersaturated with carbon dioxide at a temperature of 20° C. to 110° C. and a pressure of 30 bar to 300 bar so that a low caffeine or caffeine-free raw coffee is obtained which meets these definitions. On the other hand, the process according to the invention yields pure crystalline caffeine as a byproduct which can be utilized in pharmacology and in the beverage industry.

Many people frequently do not tolerate coffee because of its caffeine content. Many processes have therefore been developed for the purposes of extracting the caffeine from the raw coffee and simultaneously avoiding the removal of other raw coffee components which are necessary for the development of the aroma of the coffee during roasting. The caffeine is extracted from the raw coffee because if roasted coffee is decaffeinated a loss of aroma cannot be avoided.

In one prior art decaffeination process, the raw coffee is pre-treated, for example, in that the coffee beans are hydrolyzed by means of water vapor at an increased temperature, the coffee beans are extracted in a liquid-liquid extraction process by means of solvents, e.g. methylene chloride or ethyl acetate, then the solvent is removed from the raw coffee by evaporation and thereafter the moist raw coffee is dried. In this prior art process, some solvent residues may remain in the coffee and the raw coffee may be denatured to a certain extent.

Processes have also been proposed which use other solvents that need not be removed from the decaffeinated raw coffee. Of practical significance are primarily those processes which use water, supercritical carbon dioxide, liquid carbon dioxide or higher organic fatty acids (coffee oil) originating from coffee as solvents. These processes require long periods of extraction to remove caffeine to a sufficient degree. The reason for this is that the caffeine must first diffuse to the surface of the coffee beans in order to be taken up by the solvent. This process becomes slower and slower with decreasing caffeine concentration in the coffee beans. In many of these prior art processes, the solvent is circulated during the extraction process, thus causing high investment and energy costs.

DE-OS 3713953A1 which corresponds to U.S. Pat. No. 5,089,280 issued Feb. 18, 1992, discloses a process for decaffeinating raw coffee which essentially avoids the stated drawbacks. In this process, the raw coffee is moistened to a high water content of 35 to 50 weight percent and is then kept for a few minutes to several hours at a temperature of 20° to 80° C. in a gas atmosphere of 75 to 300 bar and stirred, if required. Thereafter, the pressure is reduced suddenly or within a few minutes, while avoiding freezing, to between 1 bar and $p_c$ ($p_c$ = critical pressure of the gas employed). To obtain a selective extraction of the caffeine, the raw coffee is rinsed with water or with the supercritical gas and the process is repeated several times if necessary. Thereafter, the raw coffee is pre-dried in a centrifuge and roasted. The caffeine is recovered from the rinsing agent in a known manner. This process requires a complicated and cost intensive repeated build-up of the pressure atmosphere.

SUMMARY OF THE INVENTION

It is the object of the invention to provide a simple, operationally reliable and economical process for the decaffeination of raw coffee which ensures a high degree of decaffeination, which avoids denaturing of the further components of the raw coffee, and which permits recovery of the caffeine.

According to the present invention the above objects are achieved by extracting the moist raw coffee beans by means of a liquid solvent that is saturated with carbon dioxide, the extraction taking place at a temperature from 20° to 110° C. and under a pressure of 30 to 300 bar for one to several hours. The pressure atmosphere is reduced abruptly or within a few minutes to between 1 bar and 10 bar. The expanded raw coffee beans are rinsed in the liquid solvent for a time period lasting between several minutes and two hours. The process of selective caffeine extraction at elevated pressure in the liquid solvent that is saturated with carbon dioxide and pressure reduction with rinsing of the coffee beans in the liquid solvent at a lower pressure is repeated, if necessary. Then the caffeine is selectively separated from the liquid solvent and is recovered in pure crystalline form.

The cause for the unexpected success of this pressure changing process is, among others, that a series of effects occur which supplement one another in an advantageous manner. For example, the water absorbed into the cells of the raw coffee beans creates a water-caffeine solution which facilitates the extraction of the caffeine. The extraction of other substances, particularly those required for developing the aroma during roasting, is reduced to a minimum.

The rapid pressure reduction results in a considerable increase in the volume of the gas previously diffused into the raw coffee beans, thus creating an expulsion effect for the caffeine-water solution to the surface of the raw coffee beans. The caffeine is selectively absorbed by the liquid phase surrounding the raw coffee and is transported away. The caffeine is selectively absorbed because, due to the advantageous features of the process, the process conditions cause the liquid phase to be saturated with the other components of the raw coffee but to be substantially caffeine-free.

The present invention differs advantageously from DE-OS 3713953A1 in that instead of using wet supercritical $CO_2$ or a mixture of supercritical $CO_2$ and a little water, a liquid solvent is used, preferably water or an aqueous solution, saturated or supersaturated with $CO_2$. The aqueous solution charged with the raw coffee components is decaffeinated in a subsequently connected apparatus by treatment with supercritical $CO_2$ and is saturated with the $CO_2$. By expanding this saturated water-$CO_2$ solution to a lower pressure, a supersaturated water-$CO_2$ solution is created which is introduced into the pressure vessels filled with raw coffee beans. Thus, the present invention differs from the prior art disclosed in DE-OS 3713953A1 in that no additional $CO_2$ circulation is required to build up the pressure atmosphere; rather only the slight $CO_2$ losses occurring during the caffeine recovery are replaced. Moreover, recompression in the present invention is considerably more economical because the compression work is done with a liquid medium (water saturated with $CO_2$) which is substantially incompressible. Additionally, the expansion in the raw coffee extraction vessels is able to be effected considerably faster than in DE-OS 3713953A1 because here the liquid medium, in contrast to the gaseous medium in DE-OS 3713953A1, makes it impossible for the container contents to freeze even if the pressure reduction occurs suddenly.

According to the invention, the process can be implemented particularly advantageously if the raw coffee beans are extracted in an aqueous solution that is supersaturated with $CO_2$ and saturated with the raw coffee components except for the caffeine at a temperature from 65° C. to 90° C. and under a pressure of 30 bar to 120 bar and are rinsed, after reduction of the pressure to 1 bar to 5 bar, in the substantially caffeine-free aqueous solution; the caffeine containing aqueous solution is decaffeinated in a subsequently connected column in supercritical $CO_2$ at 65° C. to 90° C. and 160 bar to 300 bar; the supercritical $CO_2$ phase charged with caffeine is regenerated in a further column by washing the caffeine out with water at 65° C. to 90° C. and 160 bar to 300 bar; and the caffeine obtained in the developing caffeine containing aqueous solution is recovered, for example, by reverse osmosis.

According to the invention, saturating the liquid solvent phase with $CO_2$ is particularly suitable However it is also within the scope of this invention to use any desired gas or gas mixture which behaves in such a manner with respect to its thermodynamic characteristics that it diffuses in noticeable concentrations into the cells of the raw beans which are filled with the water-caffeine solution. Wetting of the raw coffee beans to be decaffeinated can be omitted if water or an aqueous solution is employed as the liquid solvent. Otherwise, the coffee beans are wetted to between 20 weight percent and 40 weight percent and enough water is added to the liquid solvent that the raw coffee beans will be unable to dry out.

The raw coffee beans are extracted by means of the liquid solvent that has been saturated with $CO_2$ at the elevated pressure for one to six hours, depending on the type of coffee and the desired degree of decaffeination. The reduction of the pressure atmosphere may occur suddenly since it is impossible for the coffee beans to freeze. Although gaseous carbon dioxide is released during this pressure reduction process, the liquid phase—surprisingly—does not foam.

BRIEF DESCRIPTION OF THE DRAWING

The subject matter of the invention will now be described in greater detail with reference to various embodiments thereof with reference to the single figure which is a schematic representation of the sequence of one variation of the process for producing decaffeinated raw coffee.

DESCRIPTION OF THE PREFERRED EMBODIMENT

Figure 1:
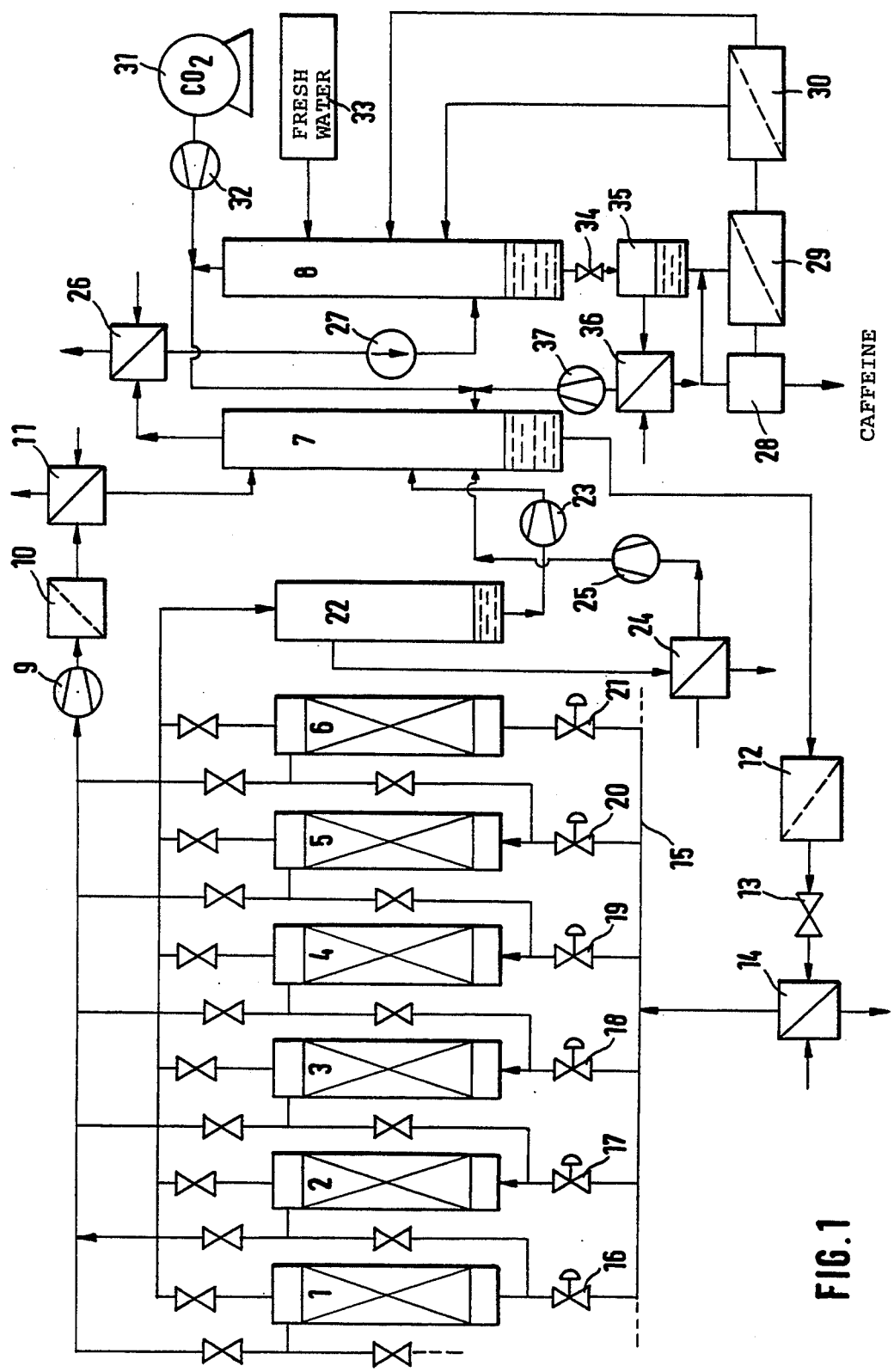

Depending on the type of coffee, the raw coffee beans are moistened with water vapor to between 20 percent by weight and 40 percent by weight and are then introduced into pressure vessels 1 to 6. The pressure vessels shown in the figure are connected in cascade so that quasi-continuous operation and thus quasi-continuous decaffeination of the raw coffee becomes possible. This also simplifies the process of moistening the coffee beans and the subsequent re-drying in that these process steps can take place substantially continuously and thus there are no long storage periods for the moistened coffee beans. Moreover, investment costs for moistening, intermediate storage and drying are lower than for a purely discontinuous procedure. The series-connected pressure vessels filled with raw coffee, for example vessels 2 to 5, are charged in such a manner with supersaturated solvent freed of caffeine that the coffee beans decaffeinated to the greatest degree are charged first. The solvent then flows through the individual vessels in the direction of increasing caffeine content of the raw coffee beans and leaves the last vessel with the maximum possible caffeine concentration.

The charged solvent phase is then introduced by means of a pump 9 through a filter stage 10 or a centrifuge (if required) and through a heat exchanger 11 (if required) into column 7 where selective extraction of the caffeine takes place at 200 bar to 300 bar and 65° C. to 110° C. as well as renewed saturation of the liquid phase with $CO_2$.

The decaffeinated solvent saturated with $CO_2$ is extracted at the bottom of column 7, is conducted through a filter stage 12 for the separation of any still existing solid particles and is expanded in a subsequent expansion valve 13 to between 30 and 100 bar, thus creating a mixture of $CO_2$ saturated solvent and $CO_2$ (supersaturated solution) which is brought to the operating temperature of the pressure vessels in a subsequently connected heat exchanger 14 and is introduced into the pressure vessels. A partial stream 15 of the $CO_2$ supersaturated solvent phase, however, is introduced through a control valve 16 to 21 into the base of a pressure vessel, for example vessel 6, whose pressure has already been reduced to between 1 bar and 5 bar, so that the caffeine enriched solvent phase there is replaced by fresh solvent. The caffeine containing solvent phase expelled, for example, into vessel 6 is fed through a degasification vessel 22 and a pump 23 into the lower portion of column 7. The $CO_2$ released in degasification vessel 22 is extracted, liquified in a condenser 24 and newly introduced into column 7 by means of a liquid gas pump 25. While vessels 2 to 5 are decaffeinated, as shown as an example in FIG. 1, at a pressure between 30 and 100 bar and vessel 6 is rinsed at a lower pressure between 1 and 5 bar, vessel 1, for example, is emptied and charged with fresh raw coffee. After closing of vessel 1, the liquid of vessel 6 is conducted to vessel 1 as soon as the rinsing process is completed and at the same time vessel 1 is ventilated by way of a ventilation valve. For the sake of clarity, the conduits and valves required for this purpose are not shown in FIG. 1. If necessary, the decaffeinated raw coffee beans in vessel 6 may be briefly rinsed with fresh water in order to avoid weight losses and possible technical difficulties during the subsequent drying process.

The process described above by way of example can be implemented in any other desired sequence or with a smaller or larger number of vessels, with the quasi-continuity of the process and thus the economy of the process increasing with increasing number of vessels. The total number of vessel reaches its optimum between 4 and 12 vessels.

The caffeine charged $CO_2$ leaving the head of column 7 is brought to the operating temperature of column 8 in a heat exchanger 26 and is introduced by means of a conveying pump 27 into the lower portion of column 8 so as to continue its circulation. In column 8, the caffeine in the caffeine charged $CO_2$ phase is substantially washed out with fresh water 33 and with substantially caffeine-free residual water obtained from the recovery of pure caffeine, for example, by way of reverse osmosis at 28 to 30. Instead of reverse osmosis, another manner of recovering the caffeine is also possible, for example, by evaporating the water. From a $CO_2$ tank 31, a pump 32 replenishes the slight $CO_2$ losses occurring during the process in the circulating $CO_2$.

Finally, the process according to the invention is distinguished by the fact that the liquid circulation (between column 7 and vessels 1 to 6) which is required for the decaffeination of the raw coffee and is, moreover, saturated with the coffee components, as well as the water circulation (between column 8, reverse osmosis 28 to 30 and fresh water 33) required for the recovery of the caffeine, are coupled together by way of a supercritical $CO_2$ phase (between column 7 and column 8). Due to the high selectivity of the supercritical carbon dioxide for caffeine, there is also no noticeable displacement and loss of the components important for developing the aroma during roasting of the raw coffee.

Preferably, columns 7 and 8 are operated isobarically and isothermally. However, with suitable temperature control, it is also possible to transfer water from one column to the next. For example, any water losses that my occur in autoclaves 1 to 6 may be compensated by a higher temperature in column 8. If, however, column 8 is operated at a lower temperature, the solvent phase in column 7 may be concentrated. The $CO_2$ obtained from the reverse osmosis during the recovery of caffeine is extracted, after expansion through a valve 34, from the subsequent degasification vessel 35, is liquefied in condenser 36 and is brought to the pressure of column 7 by means of a pump 37 to be introduced into column 7.

For example, 1000 g unroasted coffee beans having a natural moisture content of 8 weight percent and a caffeine content of 1.27 weight percent a.d. (a.d.=with reference to the dry substance) were fed into a 2.2 liter pressure vessel following the process scheme of FIG. 1. The coffee beans were extracted for four hours at a temperature of 85° C. and under a pressure of 110 bar, at a solvent flow rate of 4 kg/h by means of a substantially caffeine-free aqueous raw coffee extract that was supersaturated with $CO_2$ and included 22 weight percent dissolved coffee solids. Then the pressure atmosphere was abruptly reduced to 1 bar and the raw coffee beans were extracted for another hour by means of the raw coffee extract, with the flow rate of the substance here being 2 kg/h. The decaffeinated raw coffee extract which had previously been obtained by repeated leaching of fresh raw coffee beans at 85° C., first with fresh water and then with an aqueous solution charged with the raw coffee components decaffeinating in a spray column by treatment with supercritical $CO_2$ at 85° C. and 250 bar to a residual caffeine content of 80 ppm (mg/kg solution) caffeine, was saturated with $CO_2$ at 85° C. and 250 bar in a preceding column, its pressure was reduced to 110 bar and 1 bar, respectively, thus producing the supersaturated $CO_2$ raw coffee extract solution which was then introduced into the pressure vessel filled with coffee beans. Thereafter the swelled beans which had a moisture content of 51.6 weight percent were dried again. They had a residual caffeine content of 0.08 weight percent a.d., corresponding to a degree of decaffeination of 93.7 percent.

It will be understood that the above description of the present invention is susceptible to various modifications, changes and adaptions, and the same are intended to be comprehended within the meaning and range of equivalents of the appended claims.

What is claimed is:

1. A process for decaffeinating raw coffee beans by selective extraction of caffeine contained therein by means of a solvent that is liquid under ambient conditions, comprising the steps of
    (a) extracting the caffeine from the raw coffee beans for a period of between one to several hours by means of a liquid solvent that is comprised of water and that has been saturated with carbon dioxide at a temperature of between about 20° C. and 110° C. and at a pressure of between about 30 bar and 300 bar to provide a charged liquid solvent;
    (b) abruptly or within a few minutes reducing the pressure to between about 1 bar and about 10 bar to expand the raw coffee beans;
    (c) rinsing the expanded raw coffee beans in the liquid solvent for a period of between a few minutes to two hours;
    (d) drying the expanded raw coffee beans to reduce the water content thereof to that required for a subsequent roasting process and provide decaffeinated and pre-dried raw coffee beans;
    (e) roasting the decaffeinated and pre-dried raw coffee beans;
    (f) selectively separating the caffeine from the charged liquid solvent in a separate succeeding cycle by means of supercritical $CO_2$ and recovering the caffeine in pure crystalline form; and
    (g) reusing the decaffeinated pressurized solvent, to replace $CO_2$ losses occurring during caffeine extracting in step (a), as solvent for the extraction of caffeine and for rinsing.

2. A process as defined in claim 1, wherein steps (a), (b) and (c) are repeated.

3. A process according to claim 1, wherein the raw coffee beans to be decaffeinated are moistened to a water content of 20weight percent to 40 weight percent.

4. A process according to claim 1, wherein the liquid solvent is supersaturated with carbon dioxide.

5. A process according to claim 1, wherein the liquid solvent is water.

6. A process according to claim 1, wherein the liquid solvent is an aqueous solution which is saturated with soluble components of the raw coffee beans except for the caffeine.

7. A process according to claim 1, wherein the raw coffee beans are decaffeinated at a temperature of between 65° C. and 90° C.

8. A process according to claim 1, wherein the raw coffee beans are extracted by means of a liquid solvent which is water or an aqueous solution which has been saturated or supersaturated with carbon dioxide, and which is substantially free of caffeine, at a pressure of 30 bar to 120 bar to provide a charged liquid solvent, and wherein, after rapid expansion by reducing the pressure to between 1 bar and 5 bar, the raw coffee beans are rinsed in the same liquid solvent.

9. A process according to claim 1, carried out in a plurality of pressure autoclaves in cascade connection.

10. A process according to claim 1, wherein the charged liquid solvent is an aqueous solution charged with soluble raw coffee components including caffeine, wherein the charged liquid solvent is selectively decaffeinated by means of supercritical carbon dioxide at a temperature of 65° C. to 90° C. and at a pressure of 160 bar to 300 bar to provide a decaffeinated liquid solvent and a caffeine charged supercritical carbon dioxide phase, and wherein the decaffeinated liquid solvent is recycled and combined with raw coffee beans.

11. A process according to claim 10, further comprising regenerating the caffeine charged supercritical carbon dioxide phase at a temperature of 65° C. to 90° C. and at a pressure of 160 bar to 300 bar by washing the caffeine out with water to provide a caffeine charged aqueous phase and supercritical carbon dioxide, and wherein the supercritical carbon dioxide is recycled.

12. A process according to claim 11, further comprising treating the caffeine charged aqueous phase in a reverse osmosis system to separate same into a concentrate including 4 weight percent to 6 weight percent caffeine and a permeate including 30 ppm to 200 ppm caffeine; recovering caffeine from the concentrate by cooling it to between 0° C. and 5° C. to cause crystallization thereof and provide a mother liquor; feeding the mother liquor to the reverse osmosis system; and using the permeate to regenerate the caffeine charged supercritical carbon dioxide.

13. A process according to claim 1, wherein the steps of selectively decaffeinating the charged liquid solvent and the step of regenerating the caffeine charged supercritical carbon dioxide are carried out at the same pressure by at different temperatures so that water is caused to be transferred from one step to the other step.

14. A process for decaffeinating raw coffee beans by selective extraction of caffeine contained therein by means of a solvent that is liquid under ambient conditions, comprising the steps of:

(a) extracting the caffeine from the raw coffee beans for a period of between one to several hours by means of a liquid solvent that is comprised of water and that has been saturated with a gas or gas mixture which has such thermodynamic characteristics that it diffuses in significant concentrations into the cells of the raw coffee beans which are filled with a and aqueous caffeine solution, said extraction being carried out at a temperature of between about 20° C. to 110° C. and a pressure of between about 30 bar and 300 bar to provide a charged liquid phase;

(b) abruptly or within a few minutes reducing the pressure to between about 1 bar and about 10 bar to expand the raw coffee beans;

(c) rinsing the expanded raw coffee beans in the liquid solvent for a period of between a few minutes to two hours;

(d) drying the expanded raw coffee beans to reduce the water content thereof to that required for a subsequent roasting process and provide decaffeinated and pre-dried raw coffee beans;

(e) roasting the decaffeinated and pre-dried raw coffee beans;

(f) selectively separating the caffeine from the charged liquid solvent in a separate succeeding cycle by means of supercritical $CO_2$ and recovering the caffeine in pure crystalline form; and (g) reusing the decaffeinated pressurized solvent, to replace $CO_2$ losses occurring during caffeine extracting in step (a), as solvent for the extraction of caffeine and for rinsing.

15. A process as defined in claim 14, wherein steps (a), (b) and (c) are repeated.

* * * * *